US010387622B2

United States Patent
Hartlaub et al.

(10) Patent No.: US 10,387,622 B2
(45) Date of Patent: Aug. 20, 2019

(54) AUTOMATED MEDICATION DISPENSING UNIT AND SYSTEM FOR AN EMERGENCY MEDICAL RESPONSE VEHICLE

(71) Applicant: Aesynt Incorporated, Cranberry Township, PA (US)

(72) Inventors: Thaddeus Hartlaub, Baden, PA (US); Chad Paget, Oakdale, PA (US)

(73) Assignee: Aesynt Incorporated, Warrendale, PA (US)

( * ) Notice: Subject to any disclaimer, the term of this patent is extended or adjusted under 35 U.S.C. 154(b) by 1099 days.

(21) Appl. No.: 14/599,765

(22) Filed: Jan. 19, 2015

(65) Prior Publication Data
US 2016/0210439 A1    Jul. 21, 2016

(51) Int. Cl.
*G06F 19/00*    (2018.01)
*A61J 7/00*    (2006.01)

(52) U.S. Cl.
CPC ........ *G06F 19/3462* (2013.01); *A61J 7/0084* (2013.01); *A61J 2205/50* (2013.01); *A61J 2205/60* (2013.01)

(58) Field of Classification Search
CPC ............. G06F 19/3462; G06F 19/3456; G06F 19/3468; G06F 19/00; G06F 19/325; G06F 19/3418; G06F 19/326; G07F 11/62; G07F 17/14; G07F 5/26; G06Q 10/087; G06Q 50/24
See application file for complete search history.

(56) References Cited

U.S. PATENT DOCUMENTS

| | | | |
|---|---|---|---|
| 6,895,304 B2 | 5/2005 | Spano, Jr. et al. | |
| 7,362,228 B2 | 4/2008 | Nycz et al. | |
| 8,701,931 B2 | 4/2014 | Santmyer et al. | |
| 8,723,674 B2 | 5/2014 | Conley et al. | |
| 2008/0283596 A1 | 11/2008 | Ishida | |
| 2009/0058653 A1 | 3/2009 | Geissler et al. | |
| 2009/0071854 A1 | 3/2009 | Martin | |
| 2013/0282392 A1* | 10/2013 | Wurm | G06Q 50/22 705/2 |
| 2017/0128326 A1* | 5/2017 | Lehmann | G06F 19/3462 |
| 2017/0177832 A1* | 6/2017 | Caputo | G06F 19/3462 |

* cited by examiner

*Primary Examiner* — Maroun P Kanaan
(74) *Attorney, Agent, or Firm* — The Webb Law Firm

(57) ABSTRACT

An automated medication dispensing unit for a medical response vehicle (MRV) is provided. The unit includes a base medication dispensing unit for containing medication; a portable medication dispensing unit removeably secured to the base medication unit and containing an initial supply of medication; and a controller electronically coupled to the base medication unit and the portable medication dispensing unit which controls access to the respective base medication dispensing unit and the portable medication dispensing unit. In addition, the controller is configured for inventory management of the base medication dispensing unit and the portable medication dispensing unit. The controller may be an electronic mobile device. A method for dispensing medication from an MRV and a system for dispensing, restocking, and reordering medication are also provided.

20 Claims, 4 Drawing Sheets

AUTOMATED MEDICATION DISPENSING UNIT AND SYSTEM FOR AN EMERGENCY MEDICAL RESPONSE VEHICLE

BACKGROUND OF THE DISCLOSURE

Field of the Disclosure

The present disclosure is related to the emergency medical response field and, more particularly, to an automated medication dispensing unit for an emergency medical response vehicle (MRV). As used herein, MRV may refer to any of a number of vehicles for transporting emergency responders and other personnel to an emergency site including, but not limited to, ambulances, squads, rescue vehicles, QRS (Quick Response Vehicles), and the like. A medication dispensing system and method of dispensing medication are also provided.

Description of Related Art

MRVs are vehicles for transporting emergency responders, such as paramedics or emergency medical technicians (EMTs), and medical supplies to accident and emergency sites. An ambulance is a type of MRV that transports patients from the emergency site to a medical facility, such as a hospital. MRVs include various types of storage units for housing medical devices and medications needed for initial treatment of a patient. Some storage units are permanently attached or anchored to walls or the floor of the interior of the MRV. However, items that are needed to stabilize a patient prior to bringing him or her into the MRV are often stored in portable carriers, such as a box (e.g., a tackle box shaped unit), duffle bag, or book bag, which can be taken from the MRV and to the emergency site. For example, the portable carrier may contain medications, such as narcotics (e.g., Fentanyl or Morphine), as well as items for treating a patient, such as bandages or suture kits. Certain medications, such as narcotics, are controlled substances. Accordingly, it is important to control access and document each use of such substances, to monitor usage and prevent theft.

MRV storage units should be capable of preventing objects from falling off shelves or becoming disorganized when the MRV is in motion. For example, medical devices and medications may be stored on shelving units, lockers, drawers, or cabinets. Items may be held in place with straps, cords, clamps, and the like. Medication containers may be arranged in recesses on the shelves or may be placed in boxes, trays, or similar organizing structures. To prevent unauthorized persons from taking or using medical devices and medications, the storage units may be protected by security or locking mechanisms, such as combination locks, pad locks, bolts, chains, or cable locks. Electronic surveillance or security systems may also be used in some applications.

When the MRV arrives at an emergency site, the emergency responder removes the portable carrier from its storage location in the MRV and carries it to the patient to be treated. The portable carrier is typically prepared and stocked before arriving at the emergency site to save time upon arrival. Following treatment of the patient, the emergency responder may be responsible for documenting which items were used and for replenishing the portable carrier so that it is ready for its next use. The emergency responder may also need to provide a list of medications used to the hospital or other medical facility so that the patient may be billed correctly for medications used during treatment and so that physicians that treat the patient are aware of what medications have been previously provided.

A number of medication and medical device tracking and inventory systems are known for use in pharmacies and hospitals. These systems lack the portability required for emergency use. Such systems also are not specifically adapted for use in MRVs, ambulances, or other transport vehicles. For example, a medication dispensing cabinet is disclosed in U.S. Pat. No. 6,895,304 to Spano, Jr. et al., which is assigned to the assignee of the present application and which is incorporated by reference in its entirety. The '304 patent discloses a dispensing cabinet and method of use. The cabinet includes a number of removable shelves enclosed in a housing and accessible through a lockable door. When the dispensing cabinet is in a dispensing mode, a user can open the door and remove an item to be obtained from one of the shelves. The user may enter the number of items taken from the cabinet at a terminal for inventory purposes. The user may be required to enter an identification code to cause the locked door to open. Once the desired items are removed from the shelves, the door returns to the locked position.

U.S. Pat. No. 8,701,931 to Santmyer et al. discloses another medication dispensing cabinet. The cabinet includes a plurality of drawer assemblies. Each drawer includes a plurality of pockets covered by lids to restrict access to the interior of the pocket. A linkage or latch member engages the lids and transitions between a first state, in which the linkage member prevents the lids from being opened, and a second state in which the linkage member permits the lids to be open. The latch and linkage member may be controlled by a computer that operates a mechanism for driving the linkage, member between the locked and unlocked positions.

U.S. Pat. No. 8,723,674 to Conley et al. is directed to a tracking and inventor system that includes a medication dispensing cabinet. The cabinet is wirelessly connected to a server and computing device that can access and provide information associated with items stored in the dispensing cabinet. For example, the server and computing device may provide information about a patient's allergies, general health, or drugs previously administered. The information may be used to determine whether the drug should be provided to the patient. The cabinet may also include various sensing technologies to determine when an item is removed from the dispensing cabinet and to update inventory records accordingly.

While the above-described devices and systems assist in tracking medical items and medications, the known systems are not adapted for use in emergency response situations.

SUMMARY OF THE DISCLOSURE

In view of the foregoing, it will understood that inventorying and documenting items used during patient treatment is often time consuming and inefficient for emergency responders. Manual tracking of used items also presents opportunities for documentation errors. Therefore, it is desirable to have an automated device or system that tracks which medications or other items are used during treatment of a patient. The device or system should be integrated with other hospital information systems, such as billing and inventory management, so that the patient can be billed correctly and new items can be ordered when needed. Finally, the device or system should include a portable component or carrier that can be taken from the MRV to the emergency site for initial patient treatment. The above-described devices and systems lack any sort of a portable portion that can be used for initial treatment of a patient at an emergency site Thus, there is a need for an automated medication dispensing unit for an MRV, which includes a portable portion that can be removed from the MRV and taken to an emergency site. The dispensing unit should be capable of securely housing medication containers and other medical items while the MRV is in motion. The dispensing unit should also control access to the medications and medical items, such as by requiring a prospective user to enter an identification code or password. The dispensing unit should also be capable of documenting which items have been removed from the dispensing unit. The dispensing unit may also be integrated with a remote computer system or hospital information system and can be used to assist emergency responders and hospital personnel in dispensing, restocking, and reordering medication. The dispensing unit, methods, and systems described herein in detail address these issues.

According to one aspect, an automated medication dispensing unit for an MRV is provided. The unit includes a base medication dispensing unit for containing medication; a portable medication dispensing unit removeably secured to the base medication unit and containing an initial supply of medication; and a controller electronically coupled to the base medication unit and the portable medication dispensing unit which controls access to the respective base medication dispensing unit and the portable medication dispensing unit. In addition, the controller is configured for inventory management of the base medication dispensing unit and the portable medication dispensing unit. The controller may be an electronic mobile device.

In certain aspects of the automated medication dispensing unit, the medication is tracked by the controller via radio frequency identification (RFID) tagging of the medication. In addition, the base medication dispensing unit and the portable medication dispensing unit share a common power supply. The controller may be configured for wireless communication with a remote computer system. Furthermore, the remote computer system may include a hospital information system. The portable medication dispensing unit comprises a carrying handle for manual transportation of the portable medication dispensing unit.

The automated medication dispensing unit may also include a user interface display. The display may be removeably connected to the base medication unit and electronically coupled to the controller.

According to another aspect, a method of dispensing medication from an MRV is provided. The method includes the following steps: providing an automated medication dispensing unit in the MRV; detaching the portable medication dispensing unit from the base medication unit; dispensing medication from the portable medication dispensing unit; automatically generating data representative of the dispensed medication; and transmitting the data to a remote computer system. The automated medication dispensing unit may include a base medication dispensing unit for containing medication and a portable medication dispensing unit removeably secured to the base medication unit and containing an initial supply of medication.

In certain aspects, the method also includes the step of automatically generating a restocking order from the data for the medication dispensed from the portable medication dispensing unit. Alternatively, the method may include the steps of generating a restocking order at a restocking location from the restocking order, and restocking the portable medication dispensing unit with restocking package. The method may also include automatically assembling a purchase order from the data or transmitting the purchase order to the remote computer system. In certain aspects, the remote computer system is a hospital information system.

According to another aspect of the invention, a system for dispensing, restocking, and reordering medication for an automated medication dispensing unit for an MRV is provided. The system includes an automated medication dispensing unit for an MRV and a remote computer network configured for communication with the controller via a wireless data transmission interface. The automated medication dispensing unit includes a base medication dispensing unit for containing medication and a portable medication dispensing unit removeably secured to the base medication unit and containing an initial supply of medication. The automated medication dispensing unit also includes a controller electronically coupled to the base medication unit and the portable medication dispensing unit which controls access to the respective base medication dispensing unit and the portable medication dispensing unit. The controller is configured for inventory management of the base medication dispensing unit and the portable medication dispensing unit by automatically generating data representative of dispensed medication and transmitting the data to the remote computer network.

In certain aspects, the remote computer network is configured to receive the data transmitted by the controller and to automatically generate a restocking order from the data. In that case, the remote computer network may be configured to generate a purchase order based on the restocking order. The remote computer network may be configured to transmit at least a portion of the purchase order to a location where the purchase order can be filled. The location where the purchase order can be filled may include one or more computer workstations where the purchase order is displayed to a user.

Further details and advantages of the various aspects described in detail herein will become clear upon reviewing the following detailed description of the various aspects in conjunction with the accompanying drawing figures.

DESCRIPTION OF THE PREFERRED EMBODIMENTS

Figure 1:
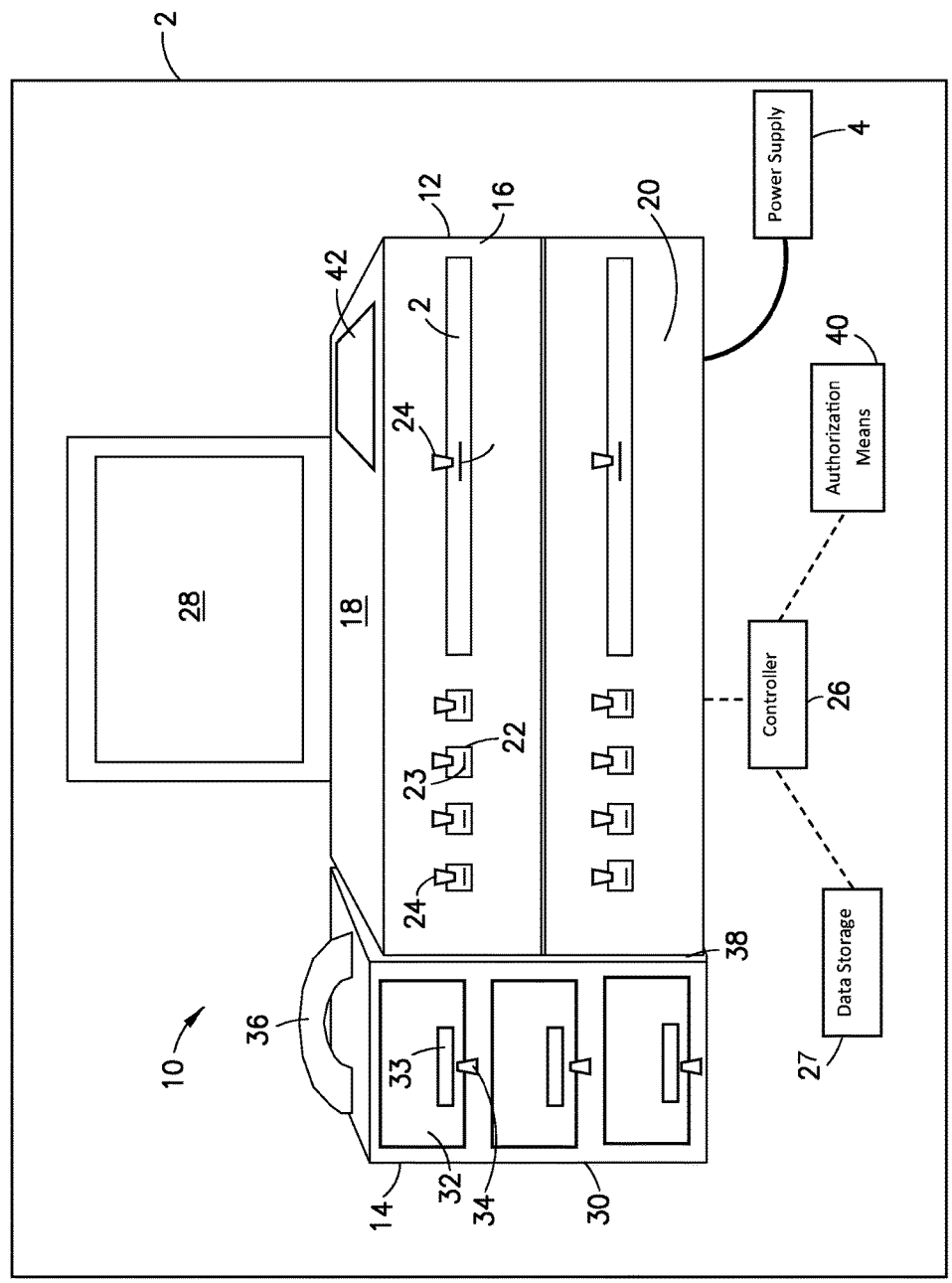
FIG. 1 is a schematic drawing of an automated medication dispensing unit.

The illustrations generally show preferred and non-limiting aspects of the systems and methods of the present disclosure. While the descriptions present various aspects of the apparatus and system, it should not be interpreted in any way as limiting the disclosure. Furthermore, modifications, concepts, and applications of the disclosure's aspects are to be interpreted by those skilled in the art as being encompassed, but not limited to, the illustrations and descriptions herein.

The following description is provided to enable those skilled in the art to make and use the described aspects contemplated for carrying out the disclosure. Various modifications, equivalents, variations, and alternatives, however, will remain readily apparent to those skilled in the art. Any and all such modifications, variations, equivalents, and alternatives are intended to fall within the spirit and scope of the present disclosure. Further, for purposes of the description hereinafter, spatial orientation terms, if used, shall relate to the disclosure as it is oriented in the drawing figures. However, it is to be understood that the disclosure may assume various alternative variations and step sequences, except where expressly specified to the contrary.

It is also to be understood that the specific devices and processes illustrated in the attached drawings, and described in the following specification, are simply exemplary aspects of the disclosure. Hence, specific dimensions and other physical characteristics related to the aspects disclosed herein are not to be considered as limiting. For the purpose of facilitating understanding of the disclosure, the accompanying drawings and description illustrate preferred aspects thereof, from which the disclosure, various aspects of its structures, construction and method of operation, and many advantages may be understood and appreciated.

With reference to FIG. 1, an automated medication dispensing unit, which is referred to hereinafter as dispensing unit 10, is illustrated. The dispensing unit 10 is configured to contain, organize, and track medication containers and other medical items that are used during treatment of a patient in emergency situations. The medication containers often include a marking or indicia on a surface thereof for identification purposes. The marking or indicia may be printed on a label affixed to the container. The label may include text describing the contents of the container, concentration, expiration dates, contraindications, or other relevant information. This information may also be presented in the form of a bar code or other machine-readable indicia. The container may also include a near-field communication item, such as a radio-frequency identification (RFID) tag that may include or be associated with relevant information. As will be described hereinafter, the dispensing unit 10 may include means for reading or tracking the medication containers by detecting and extracting information from the indicia.

The dispensing unit 10 is configured to be installed in an MRV 2 and, accordingly, includes structures for anchoring or locking the unit 10 to the floor or walls of the MRV 2. For example, in one aspect, the dispensing unit 10 may include clamps or straps for attachment to rails extending along the MRV wall. The dispensing unit 10 may also include lockable wheels and/or casters for sliding the unit 10 into the MRV 2 and locking it in place. The dispensing unit 10 may be permanently attached in the interior of the MRV 2 during manufacture of the MRV 2. Alternatively, an MRV 2 that is already in use may be retrofitted to accommodate the dispensing unit 10. The dispensing unit 10 may be connected to the MRV power supply 4, which is powered by the MRV motor. Alternatively, the dispensing unit 10 may include its own independent power supply, such as a rechargeable battery or portable generator.

The dispensing unit 10 includes a base medication dispensing unit (referred to hereinafter as base unit 12) and a portable medication dispensing unit (referred to hereinafter as portable unit 14). The base medication dispensing unit contains a large quantity of medication containers and other medical supplies and is generally used to replenish an initial supply of medication, which is stored in the portable unit 14. The larger supply of medication containers in the base unit 12 may also be used for treatment once the patient is brought into the MRV 2.

With continued reference to FIG. 1, the base unit 12 is a cabinet, chest, or box-type structure including a body 16 having an upper work surface 18 and defining an internal cavity 20. The base unit 12 includes a plurality of drawers 22 configured for slideable extension from the cabinet body 16. The drawers 22 may have a handle 23 for opening and closing the drawers 22 or may open and close automatically, such as with a motorized mechanism. The drawers 22 may have a variety of sizes and shapes. For example, narrow drawers 22 may be configured to hold a single column of identical medical containers. Wider drawers 22 may hold other arrangements of containers, such as multiple portions for holding different types or sizes of medication containers. The drawers 22 may include trays or enclosures defining recesses for holding the medication containers and other items. The drawers 22 may also include dividers that form distinct pockets sized to contain various types of medication containers. The pockets may be covered by a lid for restricting access thereto. A medication dispensing cabinet that could be used as the base unit 12 is disclosed in U.S. Pat. No. 8,701,931 to Santmyer et al., which is incorporated by reference herein in its entirety. A suitable medication dispensing cabinet is manufactured by Aesynt Incorporated, located in Cranberry, Pa., and sold under the trademark AcuDose-RX®.

In certain aspects, the base unit 12 includes a locking mechanism 24 which prevents unauthorized persons from opening the drawers 22 and removing the contents thereof. When an authorized user is identified, the locking mechanism 24 transitions to an unlocked state to allow access to the items stored in the drawer 22. For example, the locking mechanism 24 may be a mechanical latch attached to the cabinet body 16 that engages a corresponding latch on the faces of the drawers 22. The latch may be opened manually or, as is discussed in greater detail below, may be automatically controlled by a controller 26. For example, the controller 26 may be configured to provide an electronic signal to a motorized mechanism coupled to the latch that causes the latch to transition from the locked state to the unlocked state. Desirably, the latches are capable of unlocking all of the drawers 22 at the same time or of unlocking one drawer 22 at a time, while the other drawers 22 remain locked. Alternatively, or in addition to having latches connected to each drawer 22, the lids covering the pockets in each drawer 22 may include their own locking mechanisms. In this way, only certain pockets in a drawer 22 may be opened at one time to allow a user to remove specific items therefrom. Other pockets may remain locked to prevent unauthorized access or to prevent the user from accidently taking an item from the wrong pocket.

As used herein, the term controller 26 refers to an electronic device including one or more processors configured to perform operating instructions and/or to process data. The controller 26 may be a dedicated device for the dispensing unit 10. The controller 26 may also be a mobile multi-purpose electronic device, such as a computer, laptop computer, tabletPC, personal data accessory (PDA), or smartphone including instructions for operating the dispensing unit 10. The controller 26 may be integrally formed with the dispensing unit 26 or connectable via a hardwired connection through a data port or base. Alternatively, the controller 26 may be capable of accessing the automated dispensing unit 10 through a wireless Person Area Network (PAN), Local Area Network (LAN), Wide Area Network (WAN), or the Internet. In that case, the automated dispensing unit 10 includes a wireless data antenna configured to send and receive information and operating instructions from the controller 26.

The controller 26 also includes a data storage 27 for storing software and operating instructions. In addition, the data storage 27 may be capable of receiving and storing information about the operation of the dispensing unit 10 and items contained therein. For example, the data storage 27 may record the time and date that a particular user accessed the dispensing unit 10. A detailed inventory list of items contained in the dispensing unit 10 may also be recorded in the data storage 27. The data storage 27 may be any suitable computer-readable storage device including hard disks, CD-ROMs, optical storage devices, or magnetic storage devices. The data storage 27 may also be computer-readable memory in the form of secure digital (SD) memory cards, memory sticks, flash memory, or other types of removable multimedia memory cards. The data storage 27 may also be any suitable arrangement of transitory and non-transitory memory, which may include both random access memory (RAM) and read-only memory (ROM).

The controller 26 may be independently connected to the same power supply 4 as the dispensing unit 10 or may receive power directly from the dispensing unit 10. Alternatively, the controller 26 may be entirely separate from the dispensing unit 10 and include its own dedicated and independent power supply.

With continued reference to FIG. 1, the controller 26 may be associated with a visual display 28, such as a computer monitor or work station. The visual display 28 may be configured to provide a user interface that allows a user to interact with the controller 26. For example, the user interface may allow the user to select which drawers 22 or pockets should be opened. The user interface may also display inventory information, such as the number and types of medication containers remaining in the base unit 12 and/or portable unit 14, an expected time until the unit needs to be refilled, or information about when the dispensing unit 10 was last locked or unlocked. The user interface may also present information about a patient being treated, such as what medications the patient has received, when another dose should be administered, or if certain medications are contraindicated for the particular patient. As will be described hereinafter, the controller 26 may include a network interface for communication with a remote server, computer, or the Internet.

The controller 26 may also be connected to or associated with an authorization means 40. The authorization means 40 requires a prospective user to enter certain authenticating information prior to accessing the dispensing unit 10. The authorization means 40 and/or controller 26 then confirms the information to determine whether the prospective user is authorized to use the unit 10 and access the materials contained therein. The authorization means 40 may also determine that a prospective user is permitted to access certain drawers 22 or medication containers, but may restrict access to others. In one aspect, the authorization means 40 is a peripheral data entry accessory, such as a keyboard or touch screen monitor, which allows the prospective user to, enter a username, access code, or password. In other aspects, the authorization means is a biometrics system that identifies a physical feature of a prospective user. For example, a scanner may obtain an image of a fingerprint, palm print, or retina image and compare the obtained image to a prerecorded image for permitted users. Voice recognition and identification systems may also be used for this purpose.

With continued reference to FIG. 1, the portable unit 14 includes a housing 30 or body separate from the cabinet body 16 of the base unit 12 and one or more drawers 32 that slidably extend from the housing 30. The drawers 32 may include handles 33 for opening and closing. Generally, the portable unit 14 is about the shape and size of a toolbox or tackle box, which can be easily carried by a single individual. As is the case with the base unit 12, the portable unit 14 includes a locking mechanism 34, such as an automated latch, for locking the drawers 32 to prevent unauthorized access thereto. The portable unit 14 also includes a carrying handle 36 extending from a top portion thereof that can be used to lift the unit 14 from the base unit 12 and to carry the unit 14 from the MRV 2 to an emergency site. The portable unit 14 is removeably connected to the base unit 12 by another locking mechanism 38. For example, a bracket or clamp may be positioned on a side of the base unit 12. The portable unit 14 may include a connecting member configured to engage the clamp or bracket to form a removable connection therebetween. In other aspects, the base unit 12 may include a seating portion or surface that is configured to removeably receive the portable unit 14.

As was the case with the latches of the base unit 12, the locking mechanism 38 may also be associated with or connected to the controller 26 and user interface. When the authorization information is entered for the authorization means 40, the portable unit 14 may be released from the base unit 12 so that the emergency responder can take the portable unit 14 to the emergency site. When the portable unit 14 is removed, all of the drawers 32 may be automatically unlocked. In this way, the emergency responder can access the medications or other medical items contained in the portable unit 14 without needing to re-enter information in the authorization means 40 each time that another item in the portable unit 14 is needed.

Since the portable unit 14 is detachable from the base unit 12, it may include independent electronic circuitry that can be operated even when the unit 14 is not attached to the base unit 12. For example, the portable unit 14 may include an independent power supply, such as a rechargeable battery, for providing power to sensors on the unit housing 30 and the motorized mechanism that controls the latch 34 connected to the drawers 32. The rechargeable battery may be automatically recharged from the base unit 12, when connected thereto. The portable unit 14 may also include its own data storage means that collects data concerning medications removed from the unit 14 during treatment of a patient. Once the portable unit 14 is reattached to the base unit 12, the stored information about medication usage can be downloaded to the base unit 12 and processed by the controller 26 for inventory and tracking purposes. Alternatively, the portable unit 14 may include a wireless network transmission interface that transmits data about medication usage to the base unit 12 and/or controller 26 in real time.

With continued reference to FIG. 1, a variety of sensors are positioned on the base unit 12 and portable unit 14 for determining when the units 12, 14 are in a locked or unlocked state and for determining the contents of the unit 12, 14 at a particular time. For example, the locking mechanism 24 may include an optical sensor configured to visually determine the latch position. Various pressure or contact sensors could also be placed near the locking mechanism 24 and configured to determine latch position. In certain aspects, each pocket of the drawers 22 may also include a separate sensor for determining whether a pocket lid is in an open or closed position.

For determining what containers are in the units 12, 14, in one aspect, the base unit 12 includes a manual scanner 42, such as a bar code scanner or RFID reader. The user or responder is responsible for placing medication containers within close proximity to the manual scanner 42, so that the scanner can detect and extract information from the visual indicia on the container label. In other aspects, the units 12, 14 automatically identify the medication containers. For example, sensors, such as optical sensors, imaging sensors, or RFID readers, may be placed in each pocket or near the opening to each drawer. The sensors are configured to detect and identify each item placed in or removed from the pocket or drawer 22, 32. These pocket sensors may also be configured to function as fill sensors that determine the number of containers or other medical items in each pocket.

The sensors are configured to transmit data, referred to hereinafter as drawer data and medication data, to the controller 26 that is used to determine whether the drawers are open or closed and what types of medications are in the dispensing unit 10. The controller 26 may use the drawer data to modify an image on the visual display 28. For example, the visual display 28 may use the drawer data to indicate which drawers 22 or pockets are in the locked and/or unlocked position. In addition, information received from the sensors may be used to determine when certain processing routines or activities should be performed. For example, when a sensor determines that the portable unit 14 is removed from the base unit 12, the controller 26 may signal the locking mechanism 38 of the portable unit 14 to unlock the drawers 32 so that the emergency responder can easily access the containers and items therein. The controller 26 may transmit the medication data and drawer data through a network transmission interface to a remote computer network for further processing or reporting.

Figure 2:
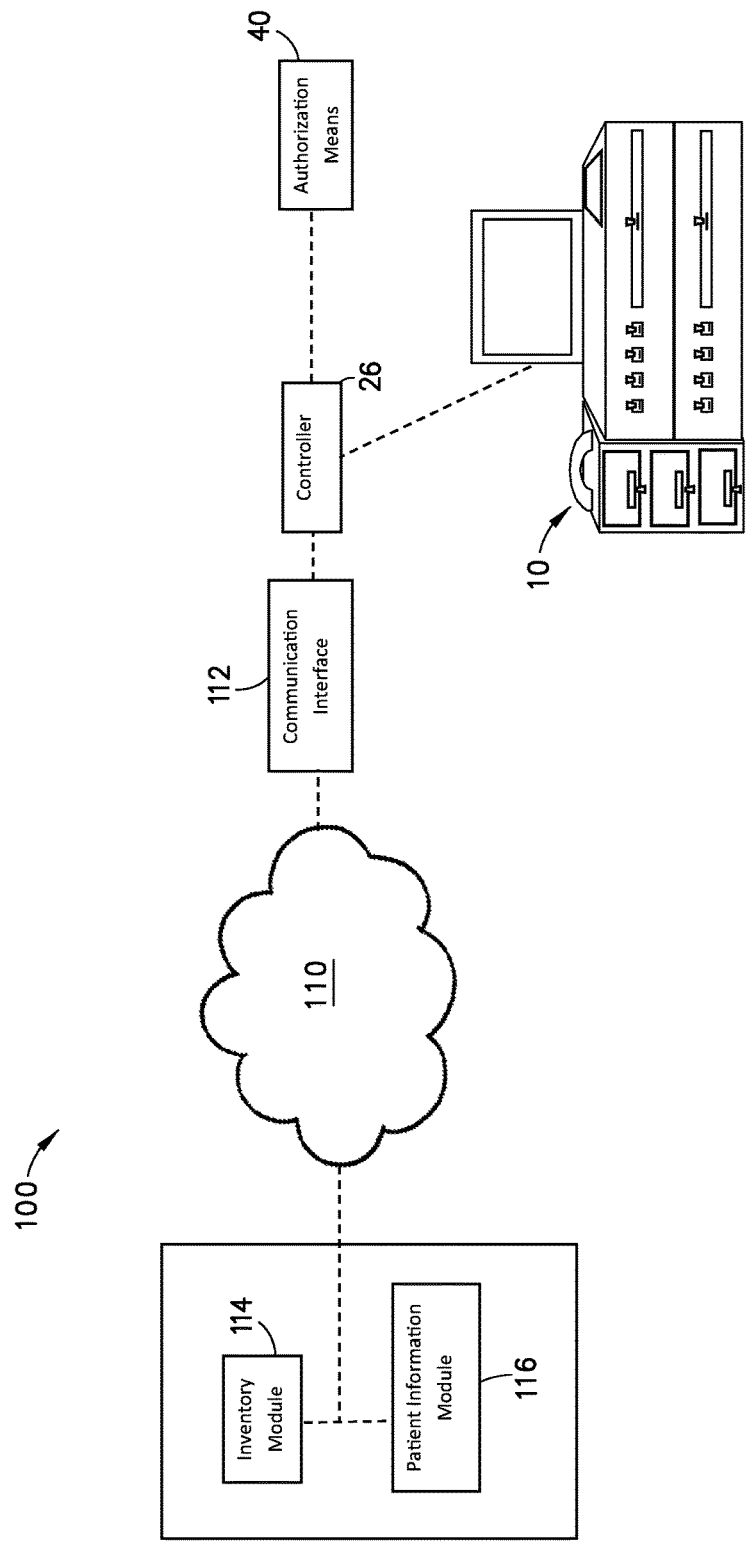
FIG. 2 is a schematic drawing of a system for dispensing medication including the automated medication dispensing unit of FIG. 1.

Having described the structure and function of the dispensing unit 10, a system 100 for dispensing, restocking, and reordering medication that includes the automated dispensing unit 10 will now be discussed in detail. With reference to FIG. 2, the system 100 includes the controller 26, automated dispensing unit 10, and a remote computer network 110. The controller 26 and remote computer network 110 are connected via a wired or wireless data communications interface 112. A wired communications interface may include various telephone (e.g. digital subscriber line (DSL)), cable, fiber, or Ethernet wired transmission protocols for sending data from the dispensing unit 10 to the remote computer network 110. A wireless communications interface may use any of a variety of known wireless data transmission protocols including, but not limited to, 802.11, general packet radio service (GPRS), Universal Mobile Telecommunications System (UMTS), Code Division Multiple Access 2000 (CDMA2000), Wideband Code Division Multiple Access (WCDMA), Time Division-Synchronous Code Division Multiple Access (TD-SCDMA), Long Term Evolution (LTE), Evolved Universal Terrestrial Radio Access Network (E-UTRAN), IEEE 802.11 (Wi-Fi), 802.16 (WiMAX), ultra wideband (UWB), infrared (IR) protocols, Bluetooth™ protocols, and/or wireless universal serial bus (USB) protocols.

As described above, the controller 26 is associated with an authorization means 40 and is configured to permit an authorized emergency responder to open and close the drawers of the base unit and portable unit when authorized by the authorization means. The controller 26 is also configured to receive information from sensors located on the dispensing unit 10. The information received from the sensors is used to determine the medication data and drawer data, in the manner described above. The controller 26 may process the medication data and drawer data to determine additional information, such as an amount of a particular medication administered to a particular patient.

The remote computer network 110, which may be colloquially referred to as 'the cloud', is a computer network capable of receiving data from the dispensing unit 10 and transmitting the received data to other elements of the network by wired or wireless means. Operating instructions, processing routines, executable computer files, and the like may also be transmitted from other system 100 elements to the dispensing unit 10 through the remote computer network 110 in the same manner. The remote computer network 110 may also include or be associated with one or more computers, servers, or data storage locations for receiving, processing, and storing data received from the dispensing unit 10 and/or other system elements. The remote computer network 110 may be accessible through a standard publicly available network protocol, such as WiFi. In that case, access to the network 110 may be limited by various security mechanisms, such as passwords, authorization codes, data encryption, and the like. Such security mechanisms may be manually entered or controlled by a user or performed automatically during data transmission by the controller 26 and/or network 110. The remote computer network 110 may also be a private wired or wireless network that is only accessible by devices configured to be connected together through the network 110.

With continued reference to FIG. 2, the remote computer network 110 may be in communication with a hospital information system, which includes one or more data storage and processing modules configured to document, store, and process information about a patient being treated at the hospital. One module is an inventory module 114. The inventory module 114 may be configured to accesses the remote computer network 110 via a wired or wireless communications interface. The inventory module 114 may be a database or server that automatically receives the medication data and drawer data. The received data is used to determine when the base unit is running low on a particular medication or medical item and, in certain aspects, may automatically reorder the depleted item. For example, the inventory module 114 may generate a restocking order including a list of needed medications. If items on the restocking order are not available at the hospital, such as in the hospital pharmacy, the inventory module 114 may generate a purchase order for needed medications and items. The purchase order may be wirelessly transmitted to an external pharmacy, shipping entity, or other location.

As described above, the medication data and drawer data may also be processed to determine an amount of a particular medication administered to a particular patient. In that case, the processed data may also be used for billing purposes. For example, the inventory module 114 may automatically generate an expense report for the patient with costs for medication used. The patient or the patient's insurance provider could then be billed for the medication provided.

The inventory module 114 may be an entirely automated system that automatically receives data, processes the data, and orders needed supplies. Alternatively, any or all of these steps may be performed by a person either in real time or at a later date, such as before a patient being treated is released from the hospital. For example, the inventory module 114 may include one or more work stations or computer terminals located at a hospital pharmacy and accessible via the remote computer network 110. The pharmacy workstation or computer may be configured to receive data from the dispensing unit 10 via the remote computer network 110. Once received, the data may cause the computer or workstation to display a message to a pharmacist. The message may instruct the pharmacist to prepare an order including items that must be replenished in the dispensing unit 10. A similar message regarding medication used may appear at a workstation located in a hospital accounting or billing department and may be used by a hospital employee to generate an expense report for the patient.

The hospital information system may also include a patient information module 116. The patient information module 116 may be configured to create or access, extract, and update information from a patient medical record maintained in an electronic database by a hospital or medical facility. As shown in FIG. 2, the patient information module 116 may receive medication data and drawer data from the dispensing unit 10 via the remote computer network 110. The patient information module 116 may be configured to automatically update the patient medical record based on the received data. The updated medical record could be provided to a treating physician once the patient arrives at the hospital. In this way, the physician would quickly know what types of treatment have already been provided to the patient. Such information may assist the physician in avoiding providing medication that has already been given to the patient or from giving a patient a drug or medication that reacts poorly with previously administered medications.

Figure 3:
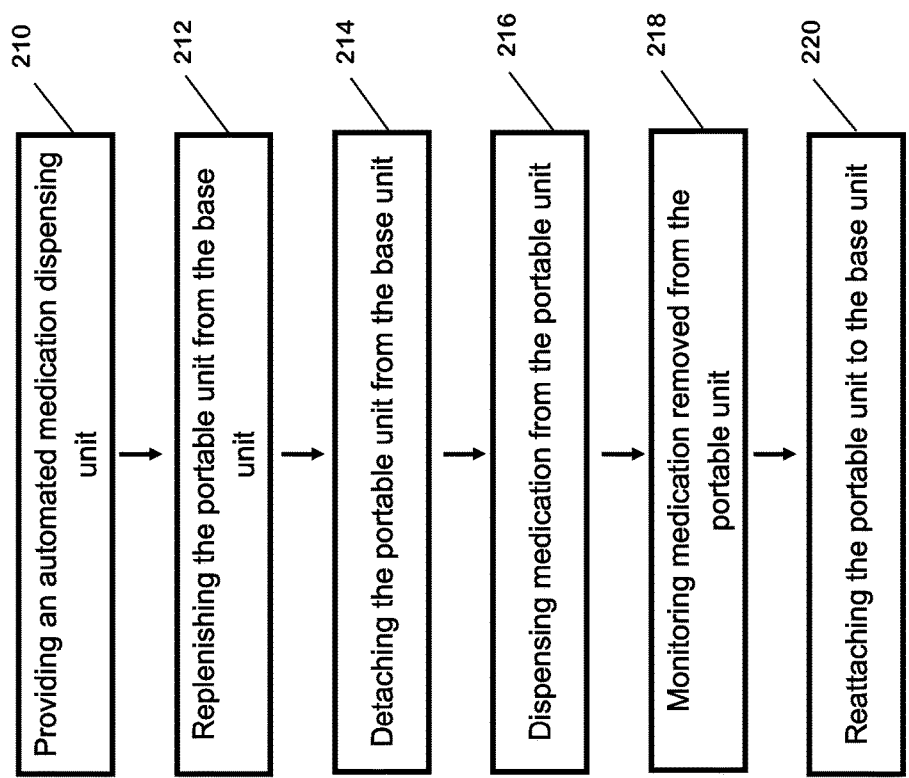
FIG. 3 is a flow chart showing a method of dispensing medication from an MRV using the automated medication dispensing unit of FIG. 1.

Having described the dispensing unit and system for dispensing, restocking, and reordering medication, methods of using the dispensing unit and system will now be discussed in detail. With reference to FIG. 3, in one aspect, the method includes providing 210 an automated medication dispensing unit. As described above, the automated medication dispensing unit includes a base unit and a portable unit. The automated dispensing unit is generally provided in a vehicle, such as an MRV. The automated dispensing unit may be installed in the MRV during manufacture of the vehicle. Alternatively, the MRV may be retrofitted to accommodate the automated dispensing unit sometime after manufacture. Prior to responding to an emergency, a responder may replenish 212 the portable unit with medication containers from the base unit. The responder may manually scan each item, using a reader or scanner, as he or she transfers it from the base unit to the portable unit. Alternatively, the responder may manually enter information about the number of medication containers transferred using a data entry accessory associated with the base unit. In other aspects, the dispensing unit automatically determines what items need to be replenished and provides this information to the responder. For example, a message may appear on a visual display associated with the dispensing unit instructing the responder to take a specific number of medication containers from the base unit and place them in an appropriate location of the portable unit. Sensors on the portable unit and base unit may be used to confirm that the correct number of medication containers were transferred.

When the MRV arrives at an emergency site, the responder detaches 214 the portable unit from the base unit. In some aspects, in order to detach the portable unit, the responder enters an authorization code using the authorization means. Alternatively, the responder allows the biometrics system to scan a portion of his or her body for authorization. Once the user is authorized, the controller causes the locking mechanism between the portable unit and base unit to release. The responder then picks up the portable unit by the carrying handle and takes the portable unit from the MRV to the emergency site to begin initial treatment of a patient.

Once at the emergency site, the responder dispenses 216 medication by opening one or more of the drawers of the portable unit to remove any needed medication containers or Other medical items from the portable unit. In some aspects, the portable unit is configured so that all of the drawers are unlocked any time that the portable unit is detached from the base unit. Accordingly, the responder is easily able to access needed items without needing to re-authenticate each time the responder opens one of the portable unit drawers.

The portable unit is configured to monitor 218 when items are taken from the portable dispensing unit. The monitoring may occur in real time. For example, the portable unit may transmit a signal to the base unit or to the remote computer network each time that an item is removed from one of the drawers. Alternatively, the portable unit may store information about what items have been removed in the data storage means associated with the portable unit. The stored data may be downloaded to the base unit or to the remote computer network at a later time, such as when the portable unit is reconnected to the base unit after the responder returns to the MRV.

Once the responder finishes an initial treatment of the patient, the patient may be transferred from the emergency site to the MRV. When the responder returns to the MRV, he or she reattaches 220 the portable unit to the base unit.

Figure 4:
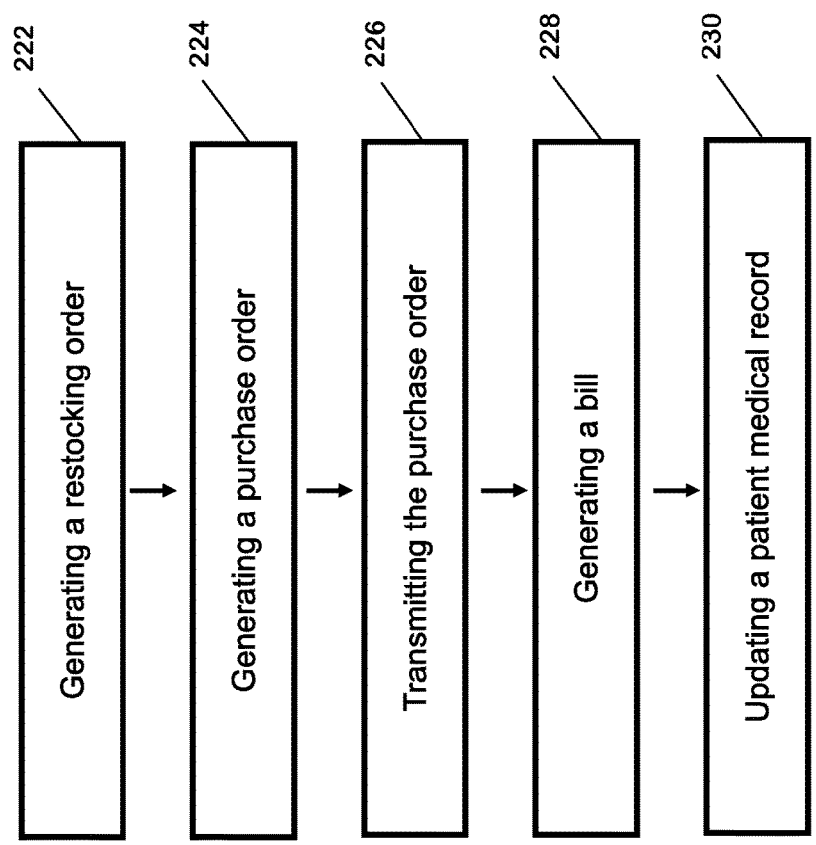
FIG. 4 is a flow chart showing a method for replenishing the automated medication dispensing unit of FIG. 1.

With reference to FIG. 4, a method for processing information received from the portable unit for inventory management purposes is provided. For example, data about the amount of medication removed from the portable unit may be used to generate a restocking order 222. The restocking order may be an itemized list of medications and other medical items that should be replenished in the portable unit prior to its next use. After the patient is transferred to the hospital, the responder may use the restocking order to assist in replenishing the portable unit with items from the base unit. If needed items are not in the base unit, the items may be obtained from a hospital pharmacy, EMT or medical supply room, or other convenient location. If needed items cannot be easily obtained, the restocking order may then be used to generate a purchase order 224 that lists needed items. The purchase order may be manually or automatically transmitted 226 to a pharmacy, drug store, or other location for filling.

The restocking order or purchase order including data indicating an amount of medication administered to the patient may also be transmitted to a hospital or emergency responder billing department. The data may be used to generate a bill 228. Similarly, data concerning medication administered to a patient may be used to update 230 the patient's medical record. The updated medical record may be provided to a treating physician at a hospital to ensure continuity of care between the emergency responder and hospital physician.

While embodiments of the automated dispensing unit, system, and method of use thereof were provided in the foregoing description, those skilled in the art may make modifications and alterations to these embodiments without departing from the scope and spirit of the disclosure. Accordingly, the foregoing description is intended to be illustrative rather than restrictive. The disclosure described hereinabove is defined by the appended claims and all changes to the disclosure that fall within the meaning and the range of equivalency of the claims are to be embraced within their scope.

The invention claimed is:

1. An automated medication dispensing unit for a medical response vehicle (MRV), comprising:
   a base medication dispensing unit for containing medication comprising a housing and at least one drawer enclosed by the housing;
   a portable medication dispensing unit removably connected to the base medication dispensing unit, the portable medication dispensing unit comprising an initial supply of medication therein, and further comprising independent electronic circuitry operable at least when the portable medication dispensing unit is detached from the base medication dispensing unit, wherein the electronic circuitry is configured to collect and store data concerning medication removed from the initial supply of medication during treatment of a patient; and
   a controller electronically coupled to the base medication dispensing unit and the portable medication dispensing unit configured to receive the data concerning medication removed from the initial supply of medication during treatment of a patient, and
   wherein the controller is further configured for inventory management of medication contained in the base medication dispensing unit and in the portable medication dispensing unit.

2. The automated medication dispensing unit for an MRV of claim 1, wherein the medication is tracked by the controller via RFID tagging of the medication.

3. The automated medication dispensing unit for an MRV of claim 1, wherein the controller is an electronic mobile device.

4. The automated medication dispensing unit for an MRV of claim 1, wherein the base medication dispensing unit and the portable medication dispensing unit share a common power supply, which provides power to the base medication dispensing unit when the base medication dispensing unit and the portable medication dispensing unit are connected together, and
   wherein the portable medication dispensing unit comprises a second power supply which provides power for the portable medication dispensing unit when the portable medication dispensing unit is not connected to the base medication dispensing unit.

5. The automated medication dispensing unit for an MRV of claim 1, wherein the controller is configured for wireless communication with a remote computer system.

6. The automated medication dispensing unit for an MRV of claim 5, wherein the remote computer system comprises a hospital information system.

7. The automated medication dispensing unit for an MRV of claim 1, wherein the portable medication dispensing unit comprises a carrying handle for manual transportation of the portable medication dispensing unit.

8. The automated medication dispensing unit for an MRV of claim 1, further comprising a user interface display removably connected to the base medication dispensing unit and electronically coupled to the controller.

9. A method of dispensing medication from a medical response vehicle (MRV), comprising:
   providing an automated medication dispensing unit in the MRV, the automated medication dispensing unit at least comprising:
      a base medication dispensing unit for containing the medication comprising a housing and at least one drawer enclosed by the housing;
      a portable medication dispensing unit removably connected to the base medication dispensing unit, the portable medication dispensing unit comprising an initial supply of medication therein, and further comprising independent electronic circuitry operable when the portable medication dispensing unit is detached from the base medication dispensing unit, wherein the electronic circuitry is configured to collect and store information concerning medication removed from the initial supply of medication during treatment of a patient;
   detaching the portable medication dispensing unit from the base medication dispensing unit;
   dispensing medication from the initial supply of medication in the portable medication dispensing unit, the electronic circuitry automatically collecting and storing data concerning the medication removed from the initial supply of medication during treatment of a patient; and
   automatically generating data representative of the medication removed from the initial supply of medication.

10. The method of claim 9, further comprising:
    automatically generating a restocking order comprising a list of medications to be restocked in the portable medication dispensing unit from the data concerning the medication removed from the initial supply of medication and at least partially restocking the portable medication dispensing unit from the base medication dispensing unit based on the restocking order.

11. The method of claim 10, further comprising:
    automatically generating a purchase order for the list of medications restocked in the portable medication dispensing unit; and
    automatically transmitting the purchase order to a remote computer system.

12. The method of claim 11, wherein the remote computer system comprises a hospital information system.

13. The method of claim 11, wherein the remote computer system comprises a hospital information system.

14. A system for dispensing, restocking, and reordering medication for an automated medication dispensing unit for a medical response vehicle (MRV), comprising:
    an automated medication dispensing unit for an MRV comprising:
       a base medication dispensing unit for containing medication comprising a housing and least one drawer enclosed by the housing; and
       a portable medication dispensing unit removably connected to the base medication dispensing unit, the portable medication dispensing unit comprising an initial supply of medication therein, and further comprising independent electronic circuitry operable at least when the portable medication dispensing unit is detached from the base medication dispensing unit, wherein the electronic circuitry is configured to collect and store data concerning medication removed from the initial supply of medication during treatment of a patient;
    a controller electronically coupled to the base medication dispensing unit and the portable medication dispensing unit configured to receive the data concerning medication removed from the initial supply of medication during treatment of a patient; and
    a remote computer network configured for wired or wireless bi-directional data communication with the controller through a data transmission interface, wherein the controller automatically generates data representative of medication dispensed from at least one of the base medication dispensing unit and the portable medication dispensing unit and transmits the data to the remote computer network for inventory management of medication contained in the base medication dispensing unit and in the portable medication dispensing unit.

15. The system of claim 14, wherein the remote computer network is configured to receive the data transmitted by the controller and to automatically generate a restocking order from the data.

16. The system of claim 15, wherein the remote computer network is configured to generate a purchase order based on the restocking order and to transmit at least a portion of the purchase order to a location where the purchase order can be filled.

17. The system of claim 16, wherein the location where the purchase order can be filled comprises one or more computer workstations where the purchase order is displayed to a user.

18. The automated medication dispensing unit for an MRV of claim 1, further comprising a lock to removably connect the portable medication dispensing unit to the base medication dispensing unit, and wherein the controller is configured to cause the lock to release the portable medication dispensing unit from the base medication dispensing unit when authorization information is received by the controller.

19. The automated medication dispensing unit of claim 18, wherein the controller is configured to automatically unlock at least one drawer of the portable medication dispensing unit when the authorization information is received by the controller.

20. The system of claim 14, further comprising a lock to removably connect the portable medication dispensing unit to the base medication dispensing unit, and wherein the controller of the automated medication dispensing unit is configured to cause the lock to release the portable medication dispensing unit from the base medication dispensing unit when authorization information is received by the controller.

* * * * *

UNITED STATES PATENT AND TRADEMARK OFFICE
CERTIFICATE OF CORRECTION

PATENT NO. : 10,387,622 B2
APPLICATION NO. : 14/599765
DATED : August 20, 2019
INVENTOR(S) : Thaddeus Hartlaub et al.

Page 1 of 1

It is certified that error appears in the above-identified patent and that said Letters Patent is hereby corrected as shown below:

In the Claims

Column 13, Line 65, Claim 9, after "containing" delete "the"

Signed and Sealed this
Twenty-ninth Day of October, 2019

Andrei Iancu
*Director of the United States Patent and Trademark Office*